(12) United States Patent
Tiwari

(10) Patent No.: US 9,265,501 B2
(45) Date of Patent: Feb. 23, 2016

(54) SURGICAL STAPLER WITH CORRUGATED THERMOPLASTIC LEAF SPRING

(75) Inventor: Anil Tiwari, Bilaspur (IN)

(73) Assignee: SABIC GLOBAL TECHNOLOGIES B.V. (NL)

( * ) Notice: Subject to any disclaimer, the term of this patent is extended or adjusted under 35 U.S.C. 154(b) by 728 days.

(21) Appl. No.: 13/604,919

(22) Filed: Sep. 6, 2012

(65) Prior Publication Data

US 2014/0061278 A1 Mar. 6, 2014

(51) Int. Cl.
*A61B 17/068* (2006.01)
*A61B 17/10* (2006.01)
*A61B 17/00* (2006.01)

(52) U.S. Cl.
CPC ............. *A61B 17/0684* (2013.01); *A61B 17/10* (2013.01); *A61B 2017/00955* (2013.01)

(58) Field of Classification Search
CPC ....... A61B 17/068; A61B 17/10; F16F 1/328; F16F 1/025; F16F 1/021; F16F 1/368
USPC ...................... 227/175.1, 176.1, 156; 267/165
See application file for complete search history.

(56) References Cited

U.S. PATENT DOCUMENTS

| 3,284,842 | A | * | 11/1966 | Jennings, Jr. .................. 16/386 |
| 3,749,389 | A | | 7/1973 | Duchemin |
| 3,945,625 | A | * | 3/1976 | Duchemin ...................... 267/47 |
| 4,256,251 | A | | 3/1981 | Moshofsky |
| 4,415,112 | A | | 11/1983 | Green |
| 4,436,201 | A | | 3/1984 | Inaba |
| 4,619,262 | A | | 10/1986 | Taylor |
| 4,648,542 | A | | 3/1987 | Fox et al. |
| 4,749,534 | A | * | 6/1988 | Robertson ..................... 264/136 |
| 5,908,149 | A | | 6/1999 | Welch et al. |
| 5,937,951 | A | | 8/1999 | Izuchukwu et al. |
| 6,066,145 | A | | 5/2000 | Wurster |

(Continued)

FOREIGN PATENT DOCUMENTS

| EP | 0167217 | 1/1986 |
| EP | 1918549 A1 | 5/2008 |

(Continued)

OTHER PUBLICATIONS

International Search Report for International Application No. PCT/IB2014/058234; International Filing Date: Sep. 5, 2013; International Mailing Date: Feb. 28, 2014; 7 Pages.

(Continued)

*Primary Examiner* — Michelle Lopez
(74) *Attorney, Agent, or Firm* — Cantor Colburn LLP

(57) ABSTRACT

A surgical stapler can comprise: a housing having side walls an end wall, a front wall, and a upper side that define a channel; a trigger; and a thermoplastic leaf spring having a proximal end and a distal end, the leaf spring comprising a non-corrugated portion and a corrugated portion. The leaf spring is attached to the trigger at the proximal end. The leaf spring extends from the trigger, through the channel toward the upper side. In an embodiment, a method for using a surgical stapler can comprise: creating relative motion between a housing and a trigger of a surgical stapler by placing a load on the surgical stapler; contacting a surface of the trigger with a cartridge comprising staple pins; releasing a staple pin from the cartridge and folding ends of the staple pin; releasing the load; and biasing the housing and trigger apart with the thermoplastic leaf spring.

18 Claims, 3 Drawing Sheets

(56) References Cited

U.S. PATENT DOCUMENTS

| | | |
|---|---|---|
| 6,601,748 B1 | 8/2003 | Fung et al. |
| 2005/0116008 A1* | 6/2005 | Thornton et al. .......... 227/176.1 |
| 2006/0033252 A1 | 2/2006 | Elmoselhy |
| 2006/0097027 A1 | 5/2006 | Brown |
| 2007/0049969 A1 | 3/2007 | Peterson |
| 2007/0213585 A1 | 9/2007 | Monassevitch et al. |
| 2007/0267792 A1 | 11/2007 | Elmoselhy |
| 2009/0294624 A1 | 12/2009 | Bechtold et al. |
| 2012/0125648 A1* | 5/2012 | Schadow et al. ................ 173/46 |

FOREIGN PATENT DOCUMENTS

| | | | |
|---|---|---|---|
| GB | 2141722 A * | 1/1985 | .............. C08L 75/04 |
| WO | 8505025 | 11/1985 | |

OTHER PUBLICATIONS

Written Opinion of the International Searching Authority for International Application No. PCT/IB2014/058234; International Filing Date: Sep. 5, 2013; International Mailing Date: Feb. 28, 2014; 7 Pages.

* cited by examiner

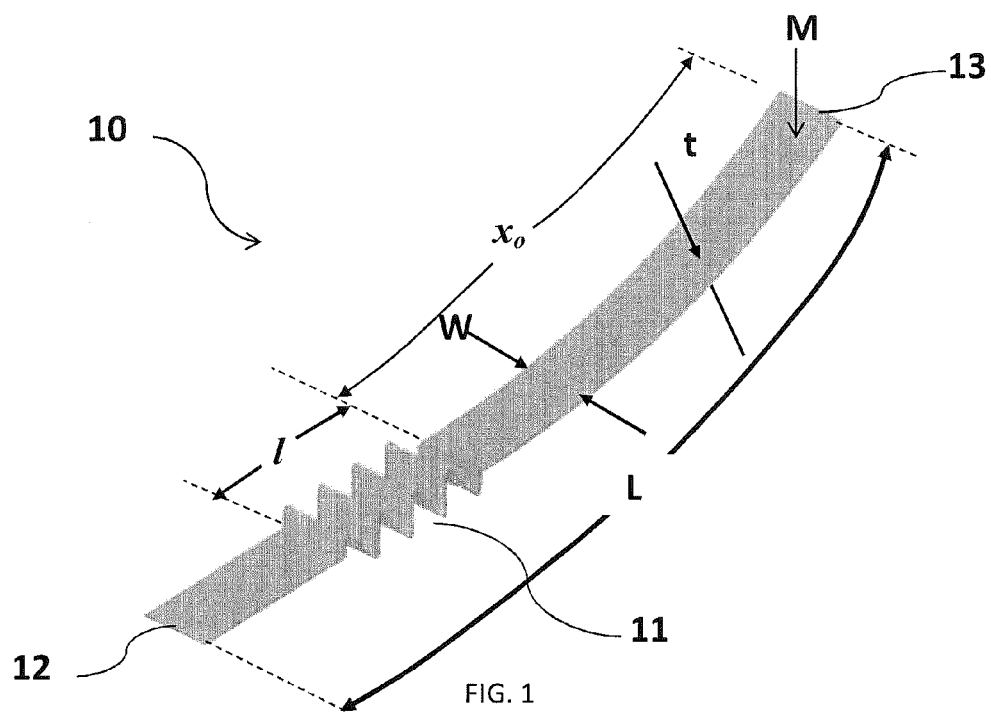
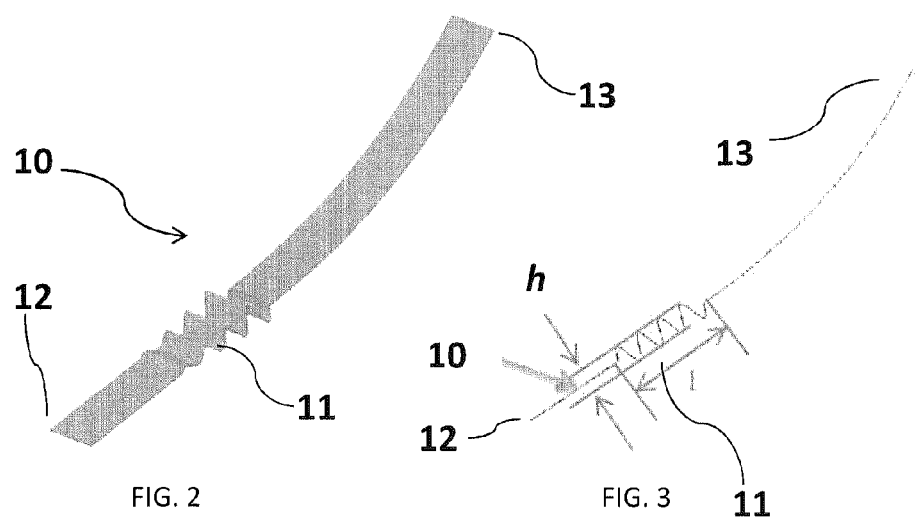
FIG. 1
FIG. 2
FIG. 3

SURGICAL STAPLER WITH CORRUGATED THERMOPLASTIC LEAF SPRING

TECHNICAL FIELD

The present disclosure relates generally to surgical staplers comprising thermoplastic corrugated leaf springs.

BACKGROUND

Surgical staplers are devices used for surgery in place of suturing to close wounds or couple tissue following incisions. Stapling can be faster, more accurate, and more consistent then suturing. In stapling, the stapler arm (e.g., the trigger) is compressed to apply the staple pin in the desired area of the tissue. As soon as the stapler's arm is released, the staple arm should be able to return to its initial configuration and be available for the next stapling action.

Currently, a metal (e.g., stainless steel) leaf spring is used to provide the stapler with the ability to return the trigger to its original position while allowing the necessary range of motion needed to activate the stapling operation upon compression. These metal leaf springs are commonly made separately, over-designed and require secondary operations (e.g., shaping of the fixed edge) to attach these springs to the stapler.

There remains a need in the art for surgical staplers that are simpler to make.

SUMMARY

Disclosed, in various embodiments, are leaf springs comprising corrugated portions capable of being coupled to components of surgical stapling devices.

In an embodiment, a surgical stapler can comprise: a housing having side walls an end wall, a front wall, and a upper side that define a channel; a trigger; and a thermoplastic leaf spring having a proximal end and a distal end, the leaf spring comprising a non-corrugated portion and a corrugated portion. The leaf spring is attached to the trigger at the proximal end. The leaf spring extends from the trigger, through the channel toward the upper side.

In an embodiment, a method for using a surgical stapler can comprise: creating relative motion between a housing and a trigger of a surgical stapler by placing a load on the surgical stapler; contacting a surface of the trigger with a cartridge comprising staple pins; releasing a staple pin from the cartridge and folding ends of the staple pin; releasing the load; and biasing the housing and trigger apart with a thermoplastic leaf spring. The leaf spring can have a proximal end and a distal end, the leaf spring comprising a non-corrugated portion and a corrugated portion, wherein the leaf spring is attached to the trigger at the proximal end, and wherein the leaf spring extends from the trigger, through a channel in the housing.

The features of the surgical stapler comprising a thermoplastic leaf spring described herein will become apparent from the following detailed description when read in conjunction with the drawings, which are exemplary, not limiting, and wherein like elements are numbered alike in several figures.

BRIEF DESCRIPTION OF THE DRAWINGS

FIG. 1 is a perspective view of an embodiment of a corrugated thermoplastic leaf spring.

FIG. 2 is a perspective view of an embodiment of a corrugated thermoplastic leaf spring showing accumulating amplitude of corrugation.

FIG. 3 is a side view of the corrugated thermoplastic leaf spring of FIG. 1.

DETAILED DESCRIPTION

Figure 4:
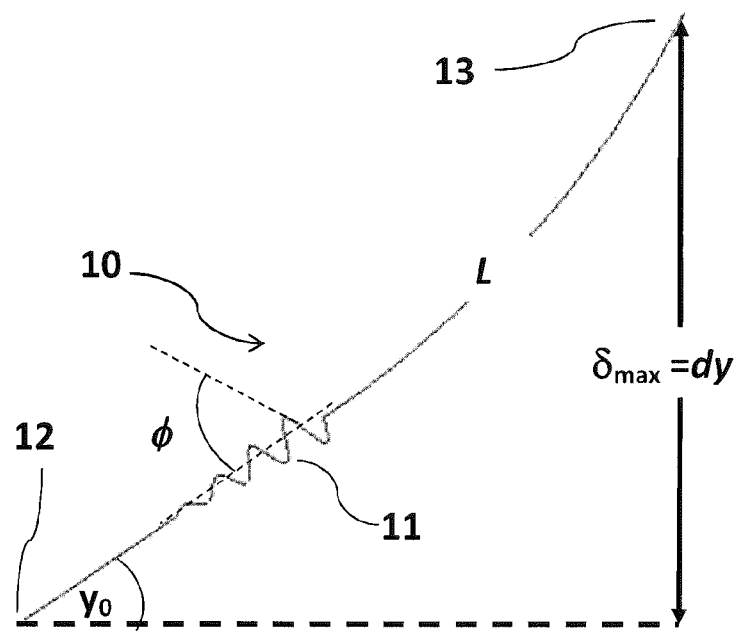
FIG. 4 is a side view of the corrugated thermoplastic leaf spring of FIG. 2.

Provided herein is a surgical stapler, with a thermoplastic leaf spring (e.g., wherein the entire trigger is formed of engineering thermoplastic (ETP)). By providing this leaf spring in a thermoplastic material, certain advantages can be derived, such as by eliminating secondary operations such as specifically adapting the metal spring to the arm and/or integration of parts, thereby reducing the number of components in the surgical stapler's trigger as well as reducing costs, assembly time, and complexity.

Under certain circumstances, the number of compression/release cycles a surgical stapler's biasing element undergoes, can be 38 (e.g., 3 cycles for testing and 35 cycles corresponding to 35 staples). A compression/release cycle of the surgical stapler's trigger may involve compression at the proper force or load. In other words, a cycle can include the application of load to: optionally cut/remove existing staple/suture/tissue; couple the edges of the tissue sought to be stapled; advance a staple; penetrate the relevant tissue with the staple; clamp the staple around the tissue; and return the trigger to its position after release. Following use, the surgical stapler is generally not reused for hygiene reasons.

The function of any biasing element (e.g., any load bearing elastic object used to store and transfer mechanical energy) in a surgical stapler, requires the flexibility to provide displacement to the full range of desired motion while simultaneously being stiff enough to provide restoring force to the surgical stapler's trigger to regain its initial spatial position. Ductile metals (e.g., stainless steel) are inherently flexible and have a Young's modulus that is high enough to give proper restoring force without reaching material plasticity (i.e. yield). Compared to metals, thermoplastic materials are less flexible and have lower Young's modulus.

Provided herein, is a thermoplastic leaf spring having a corrugated portion disposed between a proximal end and a distal end, capable of meeting performance characteristics such as flexibility to give full range of motion, for example, to a surgical stapler's trigger; and stiffness to provide proper restoring force without reaching the material plasticity threshold defined by Young's modulus.

External work done, for example by compression of the surgical stapler's trigger on such biasing element, causing it to deflect from its unstressed state, can be transformed into strain energy, referring to a form of potential energy. The strain energy in the form of elastic deformation can be recoverable in the form of mechanical work that may be used to restore the surgical stapler's trigger to its original position. For a leaf spring having a fixed proximal end, the strain energy may be described by Equation (1)

$$U = \int \frac{M^2 dy}{2EI} \quad \text{(Equ. 1)}$$

where:

U is the strain energy in Joules (J);

M is the Moment in Newton meters (Nm);

dy is the change in position of the distal end of the leaf spring in meters (m);

E is Young's modulus in Newtons per square meter (N/m$^2$); and

I is the angular moment of inertia in Newtons-meter squared (N·m$^2$) and is equal to (Wt$^3$/12), where W is the width of the leaf spring and t is its thickness (in m).

In a specific example, M can be fixed and is not related to y (e.g., when the compression force or load is applied in the same location). This can arise, for example, when the proximal end of the thermoplastic leaf spring is coupled to the surgical stapler's trigger and the distal end is slidably coupled to a housing component of the surgical stapler. Under these circumstances, Equation 1 can be written as (Equ. 1A)

$$U = \frac{M^2 L}{EI} \quad \text{(Equ. 1A)}$$

wherein L is the span of the thermoplastic leaf spring. As indicated in Equation 1, the curvature of the thermoplastic leaf spring, defines the maximum deflection obtained through bending the thermoplastic leaf spring, by determining dy, the maximum displacement possible by the distal end of the thermoplastic leaf spring upon the application of force or load.

As indicated in Equation 1, increasing the thickness of the leaf spring will affect the inertia (I). Therefore, merely increasing thickness may not help in giving proper restoring action which is dependent on the stored strain energy; and the generated stresses can cause plastic deformation (e.g., exceed Yield Stress). In addition, the stiffness of the leaf spring can be estimated by Young's modulus.

Elastic materials such as the thermoplastic leaf spring described herein, when under uniaxial compression (assuming Cartesian coordinate system; e.g., when under load only in the x direction, resulting for example, from squeezing the trigger of the surgical stapler), will tend to expand in other directions (e.g., along the y and z axes). That degree of expansion is another indication of the stiffness of the thermoplastic material and is defined as the Poisson ratio. Accordingly, varying the thickness of the corrugated portion and the selection of thermoplastic materials with proper Poisson ratio may be beneficial in providing the necessary restoring action while maintaining the durability of the thermoplastic leaf spring.

The corrugated thermoplastic leaf spring described herein can have a lower Von Mises stress at any load percent compared with a plain, non-corrugated thermoplastic leaf spring of the same span, area, thickness, and curvature.

Adding the extra material to the leaf spring in the form of corrugation can give the leaf spring the ability to store energy in the form of strain energy as described above. The stresses produced in a leaf spring with the corrugated portion can be lower for the same amount of deflection (e.g., the displacement under load of the free end of the leaf spring), than leaf spring without the corrugated portion. The thickness (t) of the leaf spring in the non-corrugated portion, length of corrugated portion (l) along the span of the leaf spring (L), the distance away from the distal end ($X_0$) where the corrugation begins, the shape of the corrugation, amplitude and thickness of the corrugated portion, are some of the design parameters that can be used to tune the desired load deflection and/or angular deflection characteristics as well as tune the proper restoring force to allow the operation of the surgical stapler comprising the thermoplastic leaf spring described herein.

The thickness ("t") of the leaf spring can be fixed or variable along the span (L) of the thermoplastic leaf spring from the proximal end to the distal end. (See FIG. 1) For example the thickness of the proximal end can be 0.8 to 4.0 mm, specifically 1.0 to 3.5 mm, more specifically 1.5 to 2.5 mm, and yet more specifically, 2.0 to 2.5 mm. Likewise, the thickness at the distal end can be, for example, 0.5 to 4.0 mm, specifically 0.5 to 3.0 mm, more specifically 1.8 to 2.2 mm, and yet more specifically, 1 to 1.5 mm. It can be beneficial to have the thickness at the proximal end, which may be coupled to the trigger of the surgical stapler, thicker than the thickness at the distal end of the thermoplastic leaf spring, wherein, for example, the thickness decreases continuously along the span of the thermoplastic leaf spring. In other words, the thermoplastic leaf spring can have a thickness that tapers continuously along the span of the thermoplastic leaf spring. The degree of tapering can be tuned to provide the desired restoring characteristics and deflection by defining a thickness ratio between the proximal end and the distal end. That ratio (e.g., the thickness of the proximal end over the thickness at the distal end) can be for example, 20:19 to 1:1, specifically, 11:10 to 2:1, more specifically 11:10 to 5:4.

Likewise, the thickness of the corrugated portion can be the same or different than the thickness of the non-corrugated portion. In other words, the corrugated portion may have a fixed thickness along the corrugation, which can be thicker, the same, or thinner than the thickness of the non-corrugated portion. For example, the thickness of the non-corrugated portion can taper as described above, while the thickness of the corrugated portion may be fixed for example at 2.0 to 3.5 mm along the length (l) of the corrugated portion. Alternatively, the thickness of the corrugated portion may vary linearly, along the length of the corrugated portion, optionally in a manner that is different than the tapering of the non-corrugated portion. The thickness of the corrugation can vary linearly from 4.0 mm at the proximal end to 1.0 mm at the distal end, specifically, from 3.0 mm at the proximal end to 1.5 mm at the distal end, and more specifically, from 2.2 mm at the proximal end to 2 mm at the distal end.

The corrugated portion is disposed such that the start of corrugation is at a distance ($X_0$) away from the distal end. The distance $X_0$ can be equal to or more than 50% of the span (L) (i.e. $X_0/L \geq 0.5$). For example, corrugation can start at a distance that is 50% to 95% of the span, specifically, 60% to 85% of the span, more specifically 67% to 75% of the span.

The length of the corrugated portion (l) may also be varied to provide an extension of the effective span (L) of the thermoplastic leaf spring as well as provide additional strain energy. For example, the length ("l") of the corrugated portion can be 2.0 to 50 mm, specifically 5.0 to 25 mm, more specifically 10 to 20 mm, and yet more specifically, 15 to 18 mm. As used herein, the length of the corrugated portion (l) refers to the length from the start of corrugation to the end of corrugation and does not include the length added due to the corrugation itself. Accordingly, while the length of the corrugated portion (l) is for example 4.0 mm, the effective length ($l_e$) provided by the corrugation itself is longer and will depend on the number of corrugations, their angle, shape, and the length of the corrugated portion (l).

The corrugated portion may have a shape defined by the development of the corrugation amplitude along the length (l) of the corrugated portion. The amplitude may be constant from the starting point near the proximal end to the distal end, an accumulating amplitude indicating an increasing amplitude from the starting point near the proximal end to the distal end as a function of the distance from the start of corrugation, or dissipating amplitude indicating a decreasing amplitude from the starting point near the proximal end to the distal end as a function of the distance from the start of corrugation. Constant amplitude can be described by Equation (2)

$$\frac{kh}{2}\mathrm{Sin}(\phi+nx_c) \qquad (\text{Equ. 2})$$

wherein:
k is an amplification constant;
h is the amplitude in mm referring to the peak-to valley height;
φ is the corrugation angle in degrees;
n is an integer representing the number of corrugations; and
$x_c$ is the distance in mm from the start of corrugation closer to the proximal end.

Likewise, accumulating amplitude can be described by Equation (3)

$$\left(\frac{kx_c}{l}\right)\frac{h}{2}\mathrm{Sin}(\phi+nx_c) \qquad (\text{Equ. 3})$$

wherein: k, h, φ, n, $x_c$ and l are as described above. Conversely, dissipating amplitude can be described by Equation (4)

$$\left(\frac{k(l-x_c)}{l}\right)\frac{h}{2}\mathrm{Sin}(\phi+nx_c) \qquad (\text{Equ. 4})$$

wherein: h, k, φ, n, $x_c$ and l are as described above.

The parameters describing the shape of the corrugation can be further used to tune the restoring force as well as the maximum deflection of the thermoplastic leaf spring. The amplitude h can be, for example, 1.0 to 10 mm, specifically, 1.5 to 7.0 mm, more specifically, 2.0 to 4.0 mm. Additionally, the amplification constant k, can be 0.2 to 2.0 and used to attenuate the amplitude along the corrugation length (l). Specifically, k, the amplification constant k, can be 0.8 to 0.3, specifically, 1. Also, φ, the corrugation angle can be for example 75 to 15 degrees, specifically 60 to 30 degrees, more specifically, 60 to 45 degrees. Likewise, n, representing the number of corrugations, can be 2 to 24 for example, specifically 3 to 12, more specifically 4 to 6.

The restoring force may also depend on the area of the thermoplastic leaf spring under load resulting from the compression of the surgical stapler's trigger. The span (L) of the thermoplastic leaf spring can be 4 to 150 mm, specifically 30 to 120 mm, more specifically 40 to 100 mm, and yet more specifically 70 to 90 mm. Also, the width (W) of the thermoplastic leaf spring can be 3.0 to 20 mm, for example, specifically 5.0 to 15 mm, more specifically 8.0 to 12 mm, e.g., 10 mm. Under certain circumstances a given ratio between the span and width of the thermoplastic leaf spring will provide the proper restoring force. That ratio can be 4:1 to 12:1, for example, specifically 5:1 to 10:1, and more specifically 7:1 to 9:1.

The thermoplastic leaf spring, as well as the surgical stapler's trigger and/or housing components, can comprise any thermoplastic material or combination of thermoplastic materials that can be formed into the desired shape and provide the desired properties. Possible materials include thermoplastic materials, as well as combinations of thermoplastic materials with elastomeric materials and/or thermoset materials. Possible thermoplastic materials include: polybutylene terephthalate (PBT); acrylonitrile-butadiene-styrene (ABS); polycarbonate; acrylic-styrene-acrylonitrile (ASA); acrylonitrile-(ethylene-polypropylene diamine modified)-styrene (AES); phenylene ether resins; polyamides; phenylene sulfide resins; polyvinyl chloride (PVC); polystyrene (e.g., high impact polystyrene (HIPS)); thermoplastic olefins (TPO) (e.g., polyethylene (such as low density polyethylene (LDPE), high density polyethylene (HDPE)) and polypropylene (PP) (such as expanded polypropylene (EPP))); as well as combinations comprising at least one of the foregoing, such as blends of polyphenylene ether/polyamide; polycarbonate/PBT blends; polycarbonate/ABS blends; copolycarbonate-polyesters. For example, the plastic component can comprise Xenoy*, which is commercially available from SABIC Innovative Plastics IP B.V. Desirably, the material is an unfilled material.

The desired properties for the thermoplastic leaf spring can be obtained with a thermoplastic material having Young's modulus of 0.5 to 70 gigaPascal (GPa), for example, specifically 1.0 to 50 GPa, more specifically 1.5 to 40 GPa. For example, the Young's modulus can be greater than or equal to 1.5 GPa, specifically 1.5 to 3.0 GPa. Additionally, the material used for the thermoplastic leaf spring can have a Poisson ratio of 0.3 to 0.5. Desirably, the material has a yield stress of greater than or equal to 60 megaPascal (MPa) (e.g., 65 to 85 MPa, specifically 75 MPa), yield strain of greater than or equal to 3% (e.g., 3% to 20%, specifically 5%), and a break strain of greater than or equal to 10% (e.g., 10% to 25%, specifically 16%).

The thermoplastic leaf spring and/or the surgical stapler's trigger and/or housing components can be manufactured utilizing various molding processes (e.g., injection molding, thermoforming, extrusion, etc.) to provide for example, a unitary piece assembly (e.g., an integrally surgical stapler trigger). In an embodiment, the thermoplastic leaf spring can be formed of a thermoplastic material that is not the same as the thermoplastic material used to form the surgical stapler's trigger; and can be operably coupled to the trigger.

A more complete understanding of the components, processes, and devices disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

FIGS. 1-4 illustrate some possible configurations of the thermoplastic leaf spring described. As shown in FIG. 1, thermoplastic leaf spring 10 of span (L), width (W) and thickness (t), comprises a corrugated portion 11 of length (l), disposed between a proximal end 12 and a distal end 13. Corrugated portion 11 starts at a distance $X_0$ from distal end 13, that is equal to or more than 50% of span (L). As shown in FIG. 3, corrugated portion 11 is a series of parallel peaks and valleys having a cross section defining a wave where the height (h) defines the vertical distance between the wave's peak and valley along the corrugated portion 11 length (l). The corrugated portion (l) is measured from the start of corrugation near the proximal end 12 to the end of corrugation toward the distal end 13. As described above and shown in FIGS. 1-4, corrugated portion 11 can have corrugations of varying shapes, for example, fixed amplitude (e.g., h=constant) along l as shown in FIGS. 1 and 3, or varying amplitude (e.g., h=f($x_c$)) along l, as shown in FIGS. 2 and 4 for accumulating amplitude (e.g., h increases from the proximal end 12 toward the distal end 13 as a function of $x_c$). FIG. 4 shows an embodiment of the thermoplastic leaf spring 10 with corrugated portion 11, having accumulating amplitude h (e.g., h=f($x_c$)) wherein distance dy defines the maximum deflection δ possible for thermoplastic leaf spring 10. Also shown is $y_0$, the constant describing the initial slope provided by the proximal end 12 coupling with the trigger 200 (shown in FIG. 5).

Figure 5:
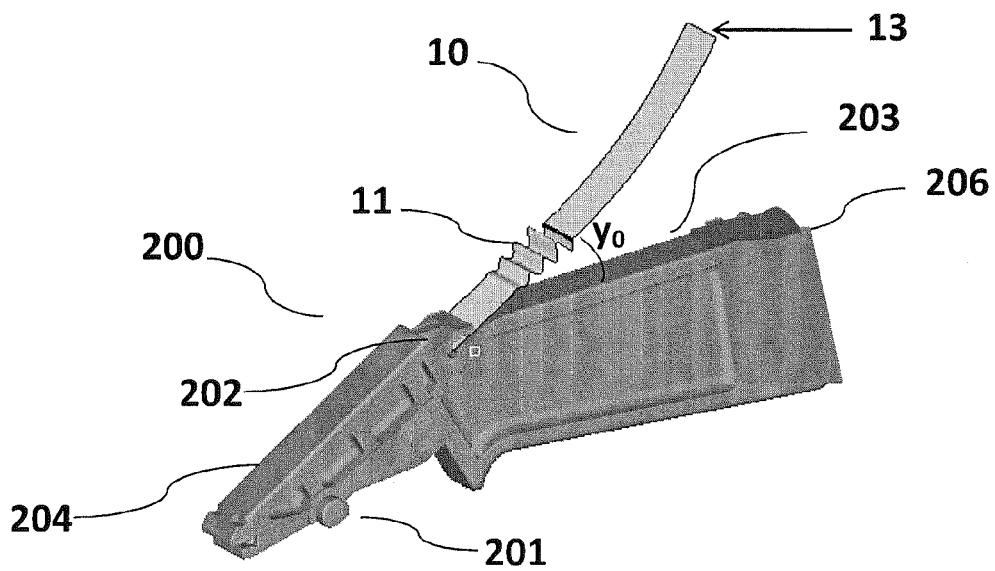
FIG. 5 is a perspective view of an embodiment of a trigger of a surgical stapler.
Figure 6:
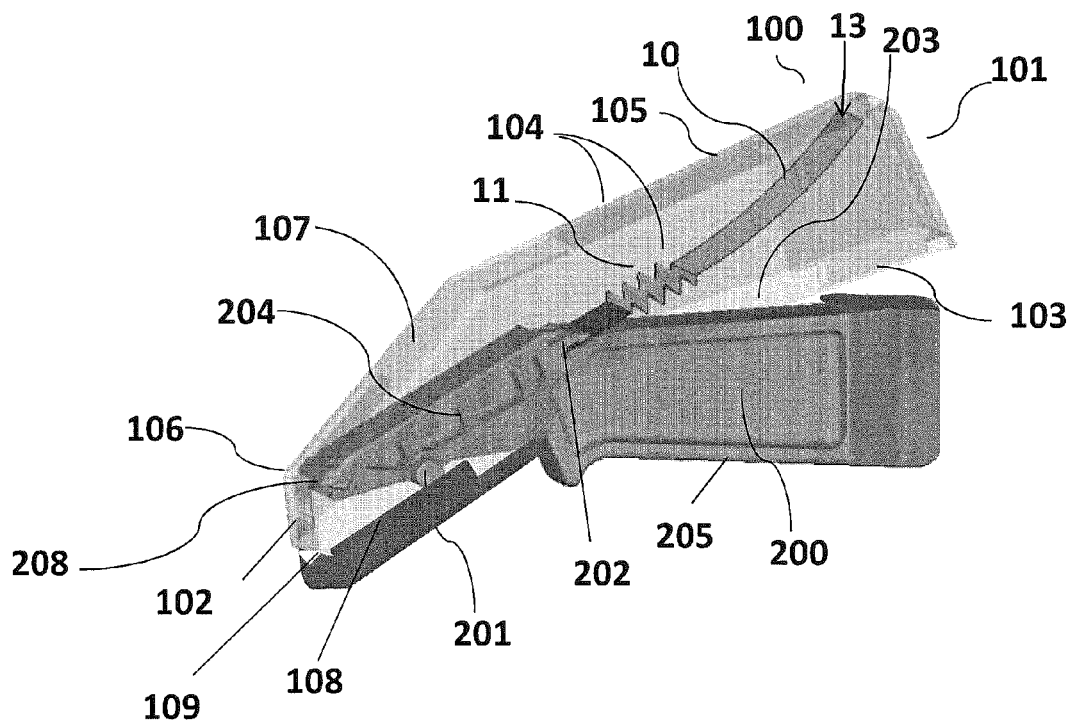
FIG. 6 is a perspective view of an embodiment of a trigger of a surgical stapler with a housing component.
Figure 7:
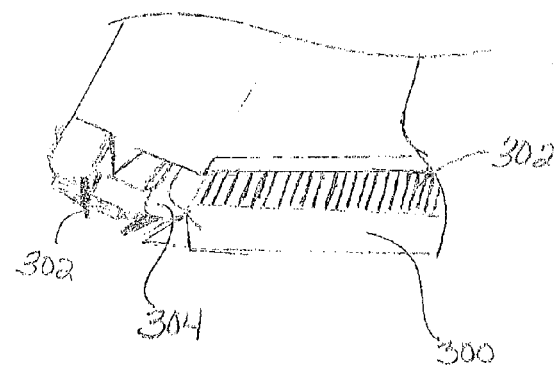
FIG. 7 is a partial perspective view of the front of the surgical stapler of FIG. 6 further illustrating the cartridge and staple pins.

Referring now to FIGS. 5-7 in the drawings. The figures illustrate an embodiment of a surgical stapling device that comprises a housing 100, which may be formed of a single component or complementary pair of components, assembled over the trigger 200. Housing 100 can be joined together by fastening elements which enable the coupling of housing parts. Housing 100 has an opening, channel 103 defined by elongated side walls 104, connected by end wall 101, front wall 102, and upper side 105. The upper side can comprise a slope 107 that decreases the size of the side walls 104 down toward the corner 106 with front wall 102. The slope 107 can be in the forward portion of the stapler, e.g., less than 50% of the distance between front wall 102 and end wall 101.

Channel 103 is configured to receive a trigger 200. As with the housing 100, the trigger 200 can be molded, for example, by thermoforming or injection molding, from an engineered thermoplastic (ETP) material. Trigger 200 can have pivot pins 201 which can engage the housing 100 to retain the housing and trigger 200 together, and to allow pivoting about the pivot pins 201. Staple cartridge 300 comprising the staple pins 302 is attached to the housing at face 108. For example, after the assembly of trigger 200 and cover 100, cartridge 300 can be bonded (e.g., glued) to the cover 100.

The leaf spring 10, is attached at the proximal end to upper edge 203 of trigger 200 with an anchor 202. The leaf spring 10 has an initial slope $y_0$, e.g., in a resting state. When the trigger 200 is assembled with the housing 100, the leaf spring 10 proximal end 12 is attached with the anchor 202 to the trigger 200, while the distal end 13 curves up toward the inner surface of upper side 105, through the channel 103. The distal end 13 abuts the upper side 105, biasing the housing 100 away from the trigger 200. The thermoplastic leaf spring 10 acts to urge the trigger 200 outwardly to the extended non-stressed position illustrated in full in FIG. 6. In this position, a nose portion 204 of trigger 200 abuts corner 106 in housing 100 to limit outward movement of the handle 207 relative to the housing 100 under the action of thermoplastic leaf spring 10. The distal end of thermoplastic leaf spring 10 is slidably engages upper surface 105 so as to be capable of sliding along the underside of the surface without being physically attached to the housing or any of its components.

During use, both the housing and trigger are grasped and squeezed together. The squeezing of these elements together forces the trigger 200 into the channel 103 of the housing 100 and forces the leaf spring 10 to flex out of its initial position to its biased position. As the trigger 200 is squeezed and moves into the channel 103, the trigger rotates about the pivot point 201. As the trigger 200 rotates about pivot pins 201 surface 208 of the trigger 200 advances towards the end point 109 (also known as the staple release area) of housing 100. When the surface 208 contacts the cartridge 300 so as to force a staple pin 302 out of the cartridge 300. While the staple pin 302 exits the stapler, pincer mechanism 304 folds ends of the staple as it passes through the area (e.g., skin tissue), so as to hold the tissue together. This movement also forces a staple to be released from the stapler through cartridge 300. Once the load is released from the housing and trigger, the leaf spring causes a relative motion between the housing and the trigger, forcing them apart, and returning the leaf spring to its resting state. For example, the leaf spring exerts a biasing force onto the upper side 105 of the housing, forcing the housing away from the trigger, and allowing the leaf spring to return to its resting state.

Examples

An embodiment of thermoplastic leaf spring described herein was compared with a plain, non-corrugated leaf spring. Thicknesses and results are shown in Table 1. For the corrugated spring, 4 corrugations were used in the simulations.

TABLE 1

| | N.C. ETP Spring thickness (mm) | | Max. Von Mises tress (MPa) | % of load | Corr. ETP Spring thickness (mm) | | | Max. Von Mises Stress (MPa) | % of load |
|---|---|---|---|---|---|---|---|---|---|
| SN | P. End | D. End | | | P. End | Corrugation | D. End | | |
| 1 | 1.50 | 1.35 | 52.94 | 38.01 | 2.0 | 1.8 | 1.8 | 38.43 | 42.16 |
| 2 | 1.80 | 1.50 | 60.13 | 52.63 | 2.2 | 2.0 | 2.0 | 41.71 | 56.76 |
| 3 | 2.40 | 2.00 | 63.58 | 100 | 2.2* | 2.2 | 2.0 | 42.77 | 66.02 |
| 4 | 2.00 | 1.80 | 67.43 | 83.2 | 2.2** | 2.2 | 2.0 | 48.50 | 75.86 |
| 5 | 2.20 | 1.80 | 68.50 | 87.11 | 2.4** | 2.2 | 2.0 | 50.78 | 85.71 | where:
SN is sample number;
N.C. ETP Spring is a non-corrugated engineering thermoplastic leaf spring;
Corr. ETP Spring is a corrugated engineering thermoplastic leaf spring;
P.End and D.End are respectively the thickness at proximal and distal ends of the leaf springs;
* Uniform amplitude corrugation as shown in FIG. 3 is used. The length of the corrugation was 16.5 mm, number of corrugations were 4, and the height of uniform amplitude corrugations were 2 mm; and
** Corrugation with varying amplitude as shown in FIG. 4 was used. The length of the corrugations was 16.5 mm, number of corrugations were 4, the height of the varying amplitude corrugations were 0.5 mm, 1.0 mm, 1.5 mm and 2.0 mm for first, second, third and fourth corrugation respectively starting from P. End.

A thermoplastic leaf spring designed as shown in FIG. 1 having a span (L) of 81.5 mm, width of 10.16 mm, and corrugated portion length (l) of 16.5 mm, made of LEXAN* polycarbonate resin, and a plain, non-corrugated LEXAN* polycarbonate leaf spring of similar dimensions have been evaluated using implicit static simulation. In the simulation, the force required to actuate the stapler is applied at the distal end of the spring in increasing incremental force and the stresses generated on the spring are examined. The percentage of load required to fully compress the spring is also monitored for different thickness for both the thermoplastic corrugated and thermoplastic plain leaf springs.

Comparative data obtained from the static simulation shows significant improvements on spring stiffness with reduced Max Von Mises stress. As shown, for example, in sample number 5, Von Mises stress in the thermoplastic leaf spring disclosed herein (50.78 MPa) is substantially lower (−26%) than the Von Mises stress experienced by the thermoplastic non-corrugated leaf spring (68.50 MPa) for similar load percent (86.36±0.75%) and thickness. Stapler load is the load applied to the trigger to cause relative motion between the trigger and the housing, to release a staple pin from the cartridge, and to fold the staple pin. The stapler load should be low enough to be applied by a human of average built and the load should be high enough to generate sufficient reaction force at the leaf spring to restore the stapler to its initial configuration. If the spring is thinner, the force required to press the stapler will be less but at the same time, the reaction force available at the leaf spring to restore the stapler will not be sufficient to restore it to initial configuration. Conversely, if the spring is thicker it will have sufficient reaction force at the leaf spring to restore the stapler to its initial configuration but the force required to press the stapler for stapling will be higher and may make the stapling inconvenient for the doctor. The stapler load depends on the size and type of stapler. In the present example the approximate value for stapler load is 1.75 pounds (lb) or 7.8 Newtons (N) which can easily be applied by a human hand and which will also generate sufficient reaction force for restoring the stapler. The load percentages are percentage of this stapler load at which staplers with different variant of corrugated leaf spring were compressed. The design criterion for the corrugated leaf spring should be to remain as close to the specified stapler load as possible with Von-Mises Stress lower than yield stress value. As shown at load percent lower than or equal to 85.71%, maximum Von Mises stress experienced by the thermoplastic corrugated leaf spring is equal to or lower than 50.78 MPa.

A surgical stapler can comprise: a housing having side walls an end wall, a front wall, and a upper side that define a channel; a trigger; and a thermoplastic leaf spring having a proximal end and a distal end, the leaf spring comprising a non-corrugated portion and a corrugated portion. The leaf spring is attached to the trigger at the proximal end. The leaf spring extends from the trigger, through the channel toward the upper side.

In an embodiment, a surgical stapler comprises a thermoplastic leaf spring having a proximal end and a distal end, the thermoplastic leaf spring comprising: a corrugated portion disposed between the proximal end and distal end, wherein the thermoplastic leaf spring is configured to bias a first component of the surgical stapler away from a second component of the surgical stapler.

In another embodiment, the first component biased by the thermoplastic leaf spring is a surgical stapler's arm, handle, trigger, staple advancing member, a staple, scission device, or a component of a surgical stapler comprising at least one of the foregoing and the second component is a boss, a surgical stapler's housing component, or a surgical stapler's component comprising at least one of the foregoing.

In an embodiment, a method for using a surgical stapler can comprise: creating relative motion between a housing and a trigger of a surgical stapler by placing a load on the surgical stapler; contacting a surface of the trigger with a cartridge comprising staple pins; releasing a staple pin from the cartridge and folding ends of the staple pin; releasing the load; and biasing the housing and trigger apart with a thermoplastic leaf spring. The leaf spring can have a proximal end and a distal end, the leaf spring comprising a non-corrugated portion and a corrugated portion, wherein the leaf spring is attached to the trigger at the proximal end, and wherein the leaf spring extends from the trigger, through a channel in the housing.

In the various embodiments: (i) the corrugated portion has a thickness that is different than the non-corrugated portion; and/or (ii) the thickness ratio between the proximal end and the distal end is 20:19 to 2:1; and/or (iii) the corrugated portion begins at a distance ($X_0$) of 50% to 95% from the distal end based on the span (L) of the surgical stapler; and/or (iv) thermoplastic material is polybutylene terephthalate; acrylonitrile-butadiene-styrene; polycarbonate; acrylic-styrene-acrylonitrile; acrylonitrile-(ethylene-polypropylene diamine modified)-styrene; phenylene ether resins; polyamides; phenylene sulfide resins; polyvinyl chloride; high impact polystyrene; thermoplastic polyolefins; or a combination comprising at least one of the foregoing; and/or (v) the thermoplastic leaf spring has Poisson Ratio of 0.3 to 0.5; and/or (vi) Young's modulus of the thermoplastic leaf spring is 0.1 to 70 GPa; and/or (vii) the thickness at the proximal end and the distal end of the thermoplastic leaf spring is 0.5 and 10 mm; and/or the span (L) of the thermoplastic leaf spring is 50 to 150 mm and the width (W) of the thermoplastic leaf spring is 2 to 20 mm; and/or (viii) the corrugated portion has a length (l) of 2 to 50 mm; and/or (ix) the corrugation amplitude in the corrugated portion is fixed, dissipating or accumulating amplitude, from the proximal end to the distal end; and/or (x) wherein the fixed amplitude is described by the equation:

$$\frac{kh}{2}\mathrm{Sin}(\phi + nx_c);$$

the dissipating amplitude is described by the equation:

$$\left(\frac{k(l-x_c)}{l}\right)\frac{h}{2}\mathrm{Sin}(\phi + nx_c)$$

and
the accumulating amplitude is described by the equation:

$$\left(\frac{kx_c}{l}\right)\frac{h}{2}\mathrm{Sin}(\phi + nx_c)$$

wherein:
$x_c$ is the distance from the start of corrugation in mm
h is 2 to 8 mm,
φ is 15 to 60 degrees,
n is an integer of 4 to 24,
k is between 0.2 to 2; and/or (xi) the thermoplastic leaf spring exhibits maximum Von Mises stress of no more than 51 MPa for a load of less than or equal to 85%; and/or (xii) the surgical stapler has fixed thickness from proximal end to distal end of 1.5 to 2.5 and exhibits maximum Von Mises stress of no more than 42 MPa for a load of less than or equal to 60%; and/or (xiii) the thermoplastic leaf spring has a 10% decrease in thickness form proximal end to distal end and exhibits maximum Von Mises stress of no more than 51 MPa for a load of less than or equal to 85%; and/or (xiv) the first component of the surgical stapler is a trigger, a handle, a staple advancing member, a staple, or a component comprising at least one of the foregoing; and/or (xv) the second component is a boss, a housing component, or a component comprising at least one of the foregoing; and/or (xvi) (a) the thermoplastic leaf spring is configured to undergo 40 to 60 compression-release cycles without increase in maximum Von Mises stress for a load of 85% of a stapler load, or (b) the thermoplastic leaf spring is configured to undergo no less than 38 compression-release cycles without increase in maximum Von Mises stress for a load of 85% of a stapler load; and/or (xvii) further comprising a cartridge comprising staple pins, wherein the cartridge is attached to the housing so that, when a load is applied to the stapler, a surface of the trigger contacts the cartridge, causing a staple pin to release from the cartridge and ends of the staple pin to be folded together; and/or (xviii) the distal end is located in the housing adjacent the upper surface; and/or (xix) the proximal end is located closer to a staple release area than the distal end.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a", "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. The term "surgical stapler" refers to any surgical stapling apparatus capable of sequentially applying a plurality of surgical fasteners to body tissue including those optionally incising the fastened tissue, whether actuated manually or by any other actuating element.

While particular embodiments have been described, alternatives, modifications, variations, improvements, and substantial equivalents that are or may be presently unforeseen may arise to applicants or others skilled in the art. Accordingly, the appended claims as filed and as they may be amended, are intended to embrace all such alternatives, modifications variations, improvements, and substantial equivalents.

What is claimed is:

1. A surgical stapler comprising:
   a housing having side walls an end wall, a front wall, and a upper side that define a channel;
   a trigger;
   a thermoplastic leaf spring having a proximal end and a distal end, the leaf spring comprising a non-corrugated portion and a corrugated portion, wherein the proximal end is located closer to a staple release area than the distal end;
   wherein the leaf spring is attached to the trigger at the proximal end;
   wherein the leaf spring extends from the trigger, through the channel toward the upper side; and
   wherein at least one of
   (i) a corrugation amplitude in the corrugated portion is dissipating amplitude or accumulating amplitude, from the proximal end to the distal end;
   (ii) the thermoplastic leaf spring exhibits maximum Von Mises stress of no more than 51 MPa for a load of 85% of a stapler load; and
   (iii) the corrugated portion has a corrugation amplitude h of 1.0 to 10 mm, an amplification constant k of 0.2 to 2.0, a corrugation angle $\phi$ of 75 to 15 degrees, and a number of corrugations of 2 to 24.

2. The surgical stapler of claim 1, wherein the corrugated portion has a thickness that is different than the non-corrugated portion.

3. The surgical stapler of claim 1, wherein a thickness ratio between the proximal end and the distal end is 20:19 to 2:1.

4. The surgical stapler of claim 1, wherein the thermoplastic material is polybutylene terephthalate; acrylonitrile-butadiene-styrene; polycarbonate; acrylic-styrene-acrylonitrile; acrylonitrile-(ethylene-polypropylene diamine modified)-styrene; phenylene ether resins; polyamides; phenylene sulfide resins; polyvinyl chloride; high impact polystyrene; thermoplastic polyolefins; or a combination comprising at least one of the foregoing.

5. The surgical stapler of claim 1, wherein the thermoplastic leaf spring has Poisson Ratio of 0.3 to 0.5.

6. The surgical stapler of claim 1, wherein Young's modulus of the thermoplastic leaf spring is 0.1 to 70 GPa.

7. The surgical stapler of claim 1, wherein a thickness at the proximal end and the distal end of the thermoplastic leaf spring is 0.5 and 10 mm.

8. The surgical stapler of claim 1, wherein the thermoplastic leaf spring has a span (L) of 50 to 150 mm and a width (W) of 2 to 20 mm.

9. The surgical stapler of claim 1, wherein the corrugated portion has a length (l) of 2 to 50 mm.

10. The surgical stapler of claim 1, wherein the corrugation amplitude is dissipating amplitude or accumulating amplitude, from the proximal end to the distal end.

11. The surgical stapler of claim 1, wherein the thermoplastic leaf spring exhibits maximum Von Mises stress of no more than 51 MPa for a load of 85% of a stapler load.

12. The surgical stapler of claim 11, wherein the surgical stapler has fixed thickness form proximal end to distal end of 1.5 to 2.5 and exhibits maximum Von Mises stress of no more than 42 MPa for a load of less than or equal to 60%.

13. The surgical stapler of claim 1, wherein the thermoplastic leaf spring has a 10% decrease in thickness from the proximal end to the distal end.

14. The surgical stapler of claim 1, wherein the corrugation amplitude h is 1.0 to 10 mm, an amplification constant k is 0.2 to 2.0, a corrugation angle $\phi$ is 75 to 15 degrees, and a number of corrugations is 2 to 24.

15. The surgical stapler of claim 1, wherein the thermoplastic leaf spring is configured to undergo 40 to 60 compression-release cycles without increase in maximum Von Mises stress for a load of 85% of a stapler load.

16. The surgical stapler of claim 1, wherein the thermoplastic leaf spring is configured to undergo no less than 38 compression-release cycles without increase in maximum Von Mises stress for a load of 85% of a stapler load.

17. A surgical stapler comprising:
- a housing having side walls an end wall, a front wall, and a upper side that define a channel;
- a trigger;
- a thermoplastic leaf spring having a proximal end and a distal end, the leaf spring comprising a non-corrugated portion and a corrugated portion, wherein the proximal end is located closer to a staple release area than the distal end;
- wherein the leaf spring is attached to the trigger at the proximal end;
- wherein the leaf spring extends from the trigger, through the channel toward the upper side;
- wherein the corrugated portion begins at a distance ($X_0$) of 50% to 95% from the distal end based on a span (L) of the surgical stapler.

18. Method for using a surgical stapler, comprising:
- creating relative motion between a housing and a trigger of a surgical stapler by placing a load on the surgical stapler;
- contacting a surface of the trigger with a cartridge comprising staple pins;
- releasing a staple pin from the cartridge and folding ends of the staple pin;
- releasing the load; and
- biasing the housing and trigger apart with a thermoplastic leaf spring having a proximal end and a distal end, the leaf spring comprising a non-corrugated portion and a corrugated portion, wherein the leaf spring is attached to the trigger at the proximal end, and wherein the leaf spring extends from the trigger, through a channel in the housing, and
- wherein at least one of
  - (i) a corrugation amplitude in the corrugated portion is dissipating amplitude or accumulating amplitude, from the proximal end to the distal end;
  - (ii) the thermoplastic leaf spring exhibits maximum Von Mises stress of no more than 51 MPa for a load of 85% of a stapler load; and
  - (iii) the corrugated portion has a corrugation amplitude h of 1.0 to 10 mm, an amplification constant k of 0.2 to 2.0, a corrugation angle φ of 75 to 15 degrees, and a number of corrugations of 2 to 24.

* * * * *